United States Patent
Herrera et al.

(10) Patent No.: US 11,992,259 B2
(45) Date of Patent: May 28, 2024

(54) FLEXIBLE MULTI-ARM CATHETER WITH DIAMETRICALLY OPPOSED SENSING ELECTRODES

(71) Applicant: Biosense Webster (Israel) Ltd., Yokneam (IL)

(72) Inventors: Kevin Justin Herrera, West Covina, CA (US); Christopher Thomas Beeckler, Brea, CA (US); Joseph Thomas Keyes, Sierra Madre, CA (US); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 524 days.

(21) Appl. No.: 17/119,949

(22) Filed: Dec. 11, 2020

(65) Prior Publication Data
US 2021/0093377 A1    Apr. 1, 2021

Related U.S. Application Data

(62) Division of application No. 15/950,994, filed on Apr. 11, 2018, now abandoned.

(51) Int. Cl.
*A61B 5/00* (2006.01)
*A61B 5/287* (2021.01)
(Continued)

(52) U.S. Cl.
CPC ........ *A61B 18/1492* (2013.01); *A61B 5/6858* (2013.01); *A61B 2018/00375* (2013.01);
(Continued)

(58) Field of Classification Search
CPC ...... A61B 18/1492; A61B 2018/00375; A61B 2018/00577; A61B 5/6858;
(Continued)

(56) References Cited

U.S. PATENT DOCUMENTS

| 4,699,147 A | 10/1987 | Chilson et al. |
| 4,940,064 A | 7/1990 | Desai |

(Continued)

FOREIGN PATENT DOCUMENTS

| CA | 3055656 A1 * | 4/2020 | ............ A61B 18/12 |
| CN | 106852690 A | 6/2017 | |

(Continued)

OTHER PUBLICATIONS

Van der Werff, H. & Heisserer, U., High-performance ballistic fibers: ultra-high molecular weight polyethylene (UHMWPE), 2016, Advanced Fibrous Composite Materials for Ballistic Protections. pp. 71-107. (Year: 2016).*

(Continued)

*Primary Examiner* — Eun Hwa Kim
(74) *Attorney, Agent, or Firm* — Troutman Pepper Hamilton Sanders LLP

(57) ABSTRACT

A medical instrument includes a shaft, multiple flexible spines and multiple electrodes. The shaft is configured for insertion into a body of a patient. The multiple flexible spines have respective first ends that are connected to a distal end of the shaft and respective second ends that are free-standing and unanchored. The spines are bent proximally such that the second ends are more proximal than the first ends. Each of the flexible spines includes a tensile layer configured to cause the flexible spine to bend proximally. The multiple electrodes are disposed over the flexible spines.

11 Claims, 3 Drawing Sheets

(51) Int. Cl.
*A61B 18/14* (2006.01)
*A61B 18/00* (2006.01)

(52) U.S. Cl.
CPC ............... *A61B 2018/00577* (2013.01); *A61B 2018/1467* (2013.01)

(58) Field of Classification Search
CPC ........ A61B 2562/043; A61B 2562/164; A61B 2562/166
See application file for complete search history.

(56) References Cited

U.S. PATENT DOCUMENTS

| | | | |
|---|---|---|---|
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,313,943 | A | 5/1994 | Houser et al. |
| 5,324,284 | A | 6/1994 | Imran |
| 5,345,936 | A | 9/1994 | Pomeranz et al. |
| 5,365,926 | A | 11/1994 | Desai |
| 5,396,887 | A | 3/1995 | Imran |
| 5,400,783 | A | 3/1995 | Pomeranz et al. |
| 5,411,025 | A | 5/1995 | Webster, Jr. |
| 5,415,166 | A | 5/1995 | Imran |
| 5,456,254 | A | 10/1995 | Pietroski et al. |
| 5,465,717 | A | 11/1995 | Imran et al. |
| 5,476,495 | A | 12/1995 | Kordis et al. |
| 5,499,981 | A | 3/1996 | Kordis |
| 5,526,810 | A | 6/1996 | Wang |
| 5,546,940 | A | 8/1996 | Panescu et al. |
| 5,549,108 | A | 8/1996 | Edwards et al. |
| 5,558,073 | A | 9/1996 | Pomeranz et al. |
| 5,577,509 | A | 11/1996 | Panescu et al. |
| 5,595,183 | A | 1/1997 | Swanson et al. |
| 5,598,848 | A | 2/1997 | Swanson et al. |
| 5,609,157 | A | 3/1997 | Panescu et al. |
| 5,628,313 | A | 5/1997 | Webster, Jr. |
| 5,681,280 | A | 10/1997 | Rusk et al. |
| 5,722,401 | A | 3/1998 | Pietroski et al. |
| 5,722,403 | A | 3/1998 | McGee et al. |
| 5,725,525 | A | 3/1998 | Kordis |
| 5,730,128 | A | 3/1998 | Pomeranz et al. |
| 5,772,590 | A | 6/1998 | Webster, Jr. |
| 5,782,899 | A | 7/1998 | Imran |
| 5,823,189 | A | 10/1998 | Kordis |
| 5,881,727 | A | 3/1999 | Edwards |
| 5,893,847 | A | 4/1999 | Kordis |
| 5,904,680 | A | 5/1999 | Kordis et al. |
| 5,911,739 | A | 6/1999 | Kordis et al. |
| 5,928,228 | A | 7/1999 | Kordis et al. |
| 5,968,040 | A | 10/1999 | Swanson et al. |
| 6,014,579 | A | 1/2000 | Pomeranz et al. |
| 6,014,590 | A | 1/2000 | Whayne et al. |
| 6,119,030 | A | 9/2000 | Morency |
| 6,216,043 | B1 | 4/2001 | Swanson et al. |
| 6,216,044 | B1 | 4/2001 | Kordis |
| 6,428,537 | B1 | 8/2002 | Swanson et al. |
| 6,456,864 | B1 | 9/2002 | Swanson et al. |
| 6,574,492 | B1 | 6/2003 | Ben-Haim et al. |
| 6,584,345 | B2 | 6/2003 | Govari |
| 6,600,948 | B2 | 7/2003 | Ben-Haim et al. |
| 6,669,693 | B2 | 12/2003 | Friedman |
| 6,738,655 | B1 | 5/2004 | Sen et al. |
| 6,741,878 | B2 | 5/2004 | Fuimaono et al. |
| 6,748,255 | B2 | 6/2004 | Fuimaono et al. |
| 6,780,183 | B2 | 8/2004 | Jimenez, Jr. et al. |
| 6,837,886 | B2 | 1/2005 | Collins et al. |
| 6,866,662 | B2 | 3/2005 | Fuimaono et al. |
| 6,892,091 | B1 | 5/2005 | Ben-Haim et al. |
| 6,970,730 | B2 | 11/2005 | Fuimaono et al. |
| 6,973,340 | B2 | 12/2005 | Fuimaono et al. |
| 6,980,858 | B2 | 12/2005 | Fuimaono et al. |
| 7,048,734 | B1 | 5/2006 | Fleischman et al. |
| 7,149,563 | B2 | 12/2006 | Fuimaono et al. |
| 7,255,695 | B2 | 8/2007 | Falwell et al. |
| 7,257,434 | B2 | 8/2007 | Fuimaono et al. |
| 7,399,299 | B2 | 7/2008 | Daniel et al. |
| 7,410,486 | B2 | 8/2008 | Fuimaono et al. |
| 7,522,950 | B2 | 4/2009 | Fuimaono et al. |
| RE41,334 | E | 5/2010 | Beatty et al. |
| 7,846,157 | B2 | 12/2010 | Kozel |
| 7,930,018 | B2 | 4/2011 | Harlev et al. |
| 8,007,495 | B2 | 8/2011 | McDaniel et al. |
| 8,048,063 | B2 | 11/2011 | Aeby et al. |
| 8,103,327 | B2 | 1/2012 | Harlev et al. |
| 8,167,845 | B2 | 5/2012 | Wang et al. |
| 8,224,416 | B2 | 7/2012 | De La Rama et al. |
| 8,235,988 | B2 | 8/2012 | Davis et al. |
| 8,346,339 | B2 | 1/2013 | Kordis et al. |
| 8,435,232 | B2 | 5/2013 | Aeby et al. |
| 8,447,377 | B2 | 5/2013 | Harlev et al. |
| 8,498,686 | B2 | 7/2013 | Grunewald |
| 8,517,999 | B2 | 8/2013 | Pappone et al. |
| 8,545,490 | B2 | 10/2013 | Mihajlovic et al. |
| 8,560,086 | B2 | 10/2013 | Just et al. |
| 8,567,265 | B2 | 10/2013 | Aeby et al. |
| 8,712,550 | B2 | 4/2014 | Grunewald |
| 8,755,861 | B2 | 6/2014 | Harlev et al. |
| 8,825,130 | B2 | 9/2014 | Just et al. |
| 8,906,011 | B2 | 12/2014 | Gelbart et al. |
| 8,945,120 | B2 | 2/2015 | McDaniel et al. |
| 8,979,839 | B2 | 3/2015 | De La Rama et al. |
| 9,037,264 | B2 | 5/2015 | Just et al. |
| 9,131,980 | B2 | 9/2015 | Bloom |
| 9,204,929 | B2 | 12/2015 | Solis |
| 9,277,960 | B2 | 3/2016 | Weinkam et al. |
| 9,314,208 | B1 | 4/2016 | Altmann et al. |
| 9,314,299 | B2 | 4/2016 | Fang |
| 9,339,331 | B2 | 5/2016 | Tegg et al. |
| 9,486,282 | B2 | 11/2016 | Solis |
| 9,554,718 | B2 | 1/2017 | Bar-Tal et al. |
| D782,686 | S | 3/2017 | Werneth et al. |
| 9,585,588 | B2 | 3/2017 | Marecki et al. |
| 9,597,036 | B2 | 3/2017 | Aeby et al. |
| 9,687,297 | B2 | 6/2017 | Just et al. |
| 9,693,733 | B2 | 7/2017 | Altmann et al. |
| 9,782,099 | B2 | 10/2017 | Williams et al. |
| 9,788,895 | B2 | 10/2017 | Solis |
| 9,801,681 | B2 | 10/2017 | Laske et al. |
| 9,814,618 | B2 | 11/2017 | Nguyen et al. |
| 9,833,161 | B2 | 12/2017 | Govari |
| 9,894,756 | B2 | 2/2018 | Weinkam et al. |
| 9,895,073 | B2 | 2/2018 | Solis |
| 9,907,609 | B2 | 3/2018 | Cao et al. |
| 9,974,460 | B2 | 5/2018 | Wu et al. |
| 9,986,949 | B2 | 6/2018 | Govari et al. |
| 9,993,160 | B2 | 6/2018 | Salvestro et al. |
| 10,014,607 | B1 | 7/2018 | Govari et al. |
| 10,028,376 | B2 | 7/2018 | Weinkam et al. |
| 10,034,637 | B2 | 7/2018 | Harlev et al. |
| 10,039,494 | B2 | 8/2018 | Altmann et al. |
| 10,045,707 | B2 | 8/2018 | Govari |
| 10,078,713 | B2 | 9/2018 | Auerbach et al. |
| 10,111,623 | B2 | 10/2018 | Jung et al. |
| 10,130,420 | B2 | 11/2018 | Basu et al. |
| 10,136,828 | B2 | 11/2018 | Houben et al. |
| 10,143,394 | B2 | 12/2018 | Solis |
| 10,172,536 | B2 | 1/2019 | Maskara et al. |
| 10,182,762 | B2 | 1/2019 | Just et al. |
| 10,194,818 | B2 | 2/2019 | Williams et al. |
| 10,201,311 | B2 | 2/2019 | Chou et al. |
| 10,219,860 | B2 | 3/2019 | Harlev et al. |
| 10,219,861 | B2 | 3/2019 | Just et al. |
| 10,231,328 | B2 | 3/2019 | Weinkam et al. |
| 10,238,309 | B2 | 3/2019 | Bar-Tal et al. |
| 10,278,590 | B2 | 5/2019 | Salvestro et al. |
| D851,774 | S | 6/2019 | Werneth et al. |
| 10,314,505 | B2 | 6/2019 | Williams et al. |
| 10,314,507 | B2 | 6/2019 | Govari et al. |
| 10,314,648 | B2 | 6/2019 | Ge et al. |
| 10,314,649 | B2 | 6/2019 | Bakos et al. |
| 10,349,855 | B2 | 7/2019 | Zeidan et al. |
| 10,350,003 | B2 | 7/2019 | Weinkam et al. |

(56) References Cited

U.S. PATENT DOCUMENTS

| | | |
|---|---|---|
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Visanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2003/0093072 A1 | 5/2003 | Friedman |
| 2004/0087848 A1 | 5/2004 | Mejia |
| 2004/0210121 A1 | 10/2004 | Fuimaono et al. |
| 2004/0243011 A1 | 12/2004 | Plaza |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0139329 A1 | 6/2011 | Clayton et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0071870 A1 | 3/2012 | Salahieh et al. |
| 2012/0172697 A1 | 7/2012 | Urman et al. |
| 2012/0271139 A1 | 10/2012 | Kordis et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0194716 A1 | 7/2014 | Diep et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2015/0351652 A1* | 12/2015 | Marecki ............ A61B 18/1492 29/829 |
| 2016/0081746 A1 | 3/2016 | Solis |
| 2016/0113582 A1 | 4/2016 | Altmann et al. |
| 2016/0113709 A1 | 4/2016 | Maor |
| 2016/0143653 A1* | 5/2016 | Vale .................. A61F 2/013 606/114 |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0055892 A1* | 3/2017 | Little .................. C12Q 1/006 |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071660 A1* | 3/2017 | Hoitink ............ A61B 18/1492 |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0112405 A1 | 4/2017 | Sterrett et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0273738 A1 | 9/2017 | Wu |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0056038 A1 | 3/2018 | Aujla |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |

(56) References Cited

U.S. PATENT DOCUMENTS

| | | |
|---|---|---|
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| CN | 111248993 A | 6/2020 |
| CN | 111248996 A | 6/2020 |
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2641556 A1 | 9/2013 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| GB | 2417836 A | 3/2006 |
| JP | 2017516588 A | 6/2017 |
| JP | 2017124159 A | 7/2017 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2016090175 A1 | 6/2016 |
| WO | 2018111600 A1 | 6/2018 |
| WO | 2018191149 A1 | 10/2018 |

(56) References Cited

FOREIGN PATENT DOCUMENTS

| WO | 2019084442 A1 | 5/2019 |
| WO | 2019143960 A1 | 7/2019 |
| WO | 2020026217 A1 | 2/2020 |
| WO | 2020206328 A1 | 10/2020 |

OTHER PUBLICATIONS

International Search Report & Written Opinion dated Aug. 6, 2019, from corresponding International Application No. PCT/IB2019/052928.
Y. Tanaka et al: "Ferrous Polycrystalline Shape-Memory Alloy Showing Huge Superelasticity", Science, vol. 327, No. 5972, Mar. 19, 2010 (Mar. 19, 2010), pp. 1488-1490, XP055226109, US ISSN: 0036-8075, DOI: 10.1126/science.1183169 abstract.
Notice of Reasons for Refusal English translation dated Jan. 24, 2023, from corresponding Japanese Application No. 2020-555334.
Notice of Reasons for Refusal English translation dated May 9, 2023, from corresponding Japanese Application No. 2020-555334.
International Preliminary Report on Patentability dated Oct. 13, 2020, from corresponding International Application No. PCT/IB2019/052928.
First Search dated Sep. 28, 2023, from corresponding Chinese Application No.: 201980024994.1.
First Office Action dated Sep. 28, 2023, from corresponding Chinese Application No.: 201980024994.1.

* cited by examiner

FLEXIBLE MULTI-ARM CATHETER WITH DIAMETRICALLY OPPOSED SENSING ELECTRODES

This divisional patent application claims the benefits of priority under 35 USC§ 120 to prior filed U.S. patent application Ser. No. 15/950,994 filed on Apr. 11, 2018, pending, which prior patent application is hereby incorporated by reference herein to this application as if set out in full.

FIELD OF THE INVENTION

The present invention relates generally to medical probes, and particularly to multi-electrode catheters.

BACKGROUND OF THE INVENTION

Various types of diagnostic-catheters and therapeutic-catheters may be used in cardiac diagnostic procedures. For example, U.S. Patent Application Publication 2016/0081746 describes a catheter adapted for mapping and/or ablation in the atria that has a basket-shaped electrode array with two or more location sensors with a deflectable expander. The catheter comprises a catheter body, a basket electrode assembly at a distal end of the catheter body, and a control handle at a proximal end of the catheter body. The basket electrode assembly has a plurality of electrode-carrying spines and an expander that is adapted for longitudinal movement relative to the catheter body for expanding and collapsing the assembly via a proximal end portion extending past the control handle that can be pushed or pulled by a user. The expander is also adapted for deflection in response to an actuator on the control handle that allows a user to control at least one puller wire extending through the catheter body and the expander.

As another example, U.S. Pat. No. 6,669,693 describes a device having a retractable and deployable umbrella body. The umbrella body includes ablation elements for circumferentially engaging and ablating a target tissue. The umbrella body is an adjustable, compliant cone-shaped member that may be deployed over a wide range of working diameters. The ablation elements are attached to spines and to a circumferential loop or loop segment attached to the spines. The ablation elements attached to the umbrella body can therefore conform to the geometry of the pulmonary vein ostium and provide circumferential contact, which permits more accurate ablation procedures.

International Patent Application Publication WO/2016/090175 (PCT/US2015/063807) describes in various embodiments, systems, devices and methods for modulating targeted nerve fibers (e.g., hepatic neuromodulation) or other tissue. The systems may be configured to access tortuous anatomy of or adjacent hepatic vasculature. The systems may be configured to target nerves surrounding (e.g., within adventitia of or within perivascular space of) an artery or other blood vessel, such as the common hepatic artery.

U.S. Patent Application Publication 2012/0172697 describes a medical device that has a flexible elongated body, a handle connected to the elongated body, at least one spine connected to the elongated body, and a flexible sheet attached to the at least one spine. The flexible sheet has a plurality of electrodes thereon, wherein the flexible sheet and the plurality of electrodes define a mapping assembly for mapping electrical information in tissue, and wherein the at least one spine and the flexible sheet is movable from a collapsed configuration to a deployed configuration.

SUMMARY OF THE INVENTION

An embodiment of the present invention provides a medical instrument including a shaft, multiple flexible spines and multiple electrodes. The shaft is configured for insertion into a body of a patient. The multiple flexible spines have respective first ends that are connected to a distal end of the shaft and respective second ends that are free-standing and unanchored. The spines are bent proximally such that the second ends are more proximal than the first ends. Each of the flexible spines includes a tensile layer configured to cause the flexible spine to bend proximally. The multiple electrodes are disposed over the flexible spines.

In some embodiments, the multiple electrodes are disposed over diametrically opposing surfaces of the flexible spines.

In some embodiments, the flexible spines and the electrodes include circuit board substrates, and metallic elements disposed on the circuit board substrates, respectively. In some embodiments, the circuit board substrates are folded so that the multiple electrodes are disposed over diametrically opposing facets of the circuit board substrates.

In an embodiment, each of the tensile layers includes one or more tensile fibers configured to cause the flexible spine to bend proximally. In another embodiment, a tensile strength of the layer is greater than that of a Nitinol alloy layer of same dimensions. In one example, the tensile strength of the layer is greater than the ultimate tensile strength of fully annealed Nitinol (at approximately 895 MPa) and greater than the tensile strength of work hardened Nitinol (at approximately 1900 MPa).

There is additionally provided, in accordance with an embodiment of the present invention, a manufacturing method, including producing multiple flexible spines having multiple electrodes disposed thereon. The multiple flexible spines are mounted at a distal end of a shaft. The multiple flexible spines have respective first ends that are connected to a distal end of the shaft and respective second ends that are free-standing and unanchored, and the spines are bent proximally such that the second ends are more proximal than the first ends.

There is also provided, in accordance with an embodiment of the present invention, a manufacturing method, including patterning electrodes and conductive lines on multiple flexible circuit boards. Pairs of the flexible circuit boards are laminated with a layer of tensile material sandwiched between the circuit boards of each pair, so as to form flexible spines. The multiple flexible spines are mounted at a distal end of a shaft. The multiple flexible spines have respective first ends that are connected to a distal end of the shaft and respective second ends that are free-standing and unanchored, and the spines are bent proximally such that the second ends are more proximal than the first ends. A tensile layer included in each of the flexible spines is configured to cause the flexible spines to bend proximally.

There is further provided, in accordance with an embodiment of the present invention, a manufacturing method, including patterning electrodes and conductive lines on multiple flexible circuit boards. The flexible circuit boards are folded along respective longitudinal axes of the circuit boards, over one or more fibers made of a tensile material, such that the fibers become sandwiched between two diametrically opposing facets of the patterned flexible boards, so as to form flexible spines. The multiple flexible spines are mounted at a distal end of a shaft. The multiple flexible spines have respective first ends that are connected to a distal end of the shaft and respective second ends that are free-standing and unanchored, and the spines are bent proximally such that the second ends are more proximal than the first ends. A tensile layer included in each of the flexible spines is configured to cause the flexible spines to bend proximally.

The present invention will be more fully understood from the following detailed description of the embodiments thereof, taken together with the drawings in which:

DETAILED DESCRIPTION OF EMBODIMENTS

Overview

Figure 1:
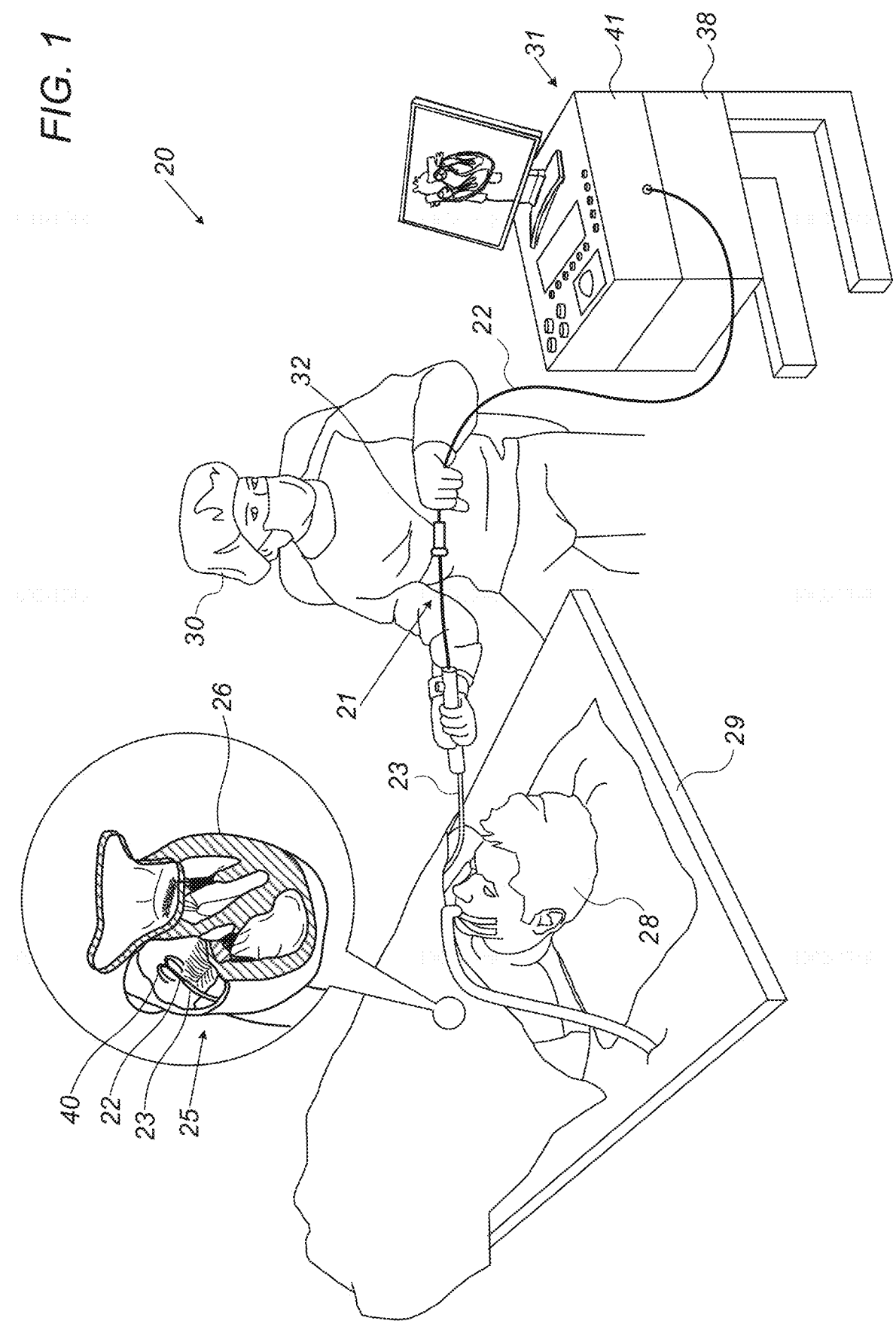
FIG. 1 is a schematic, pictorial illustration of a catheter-based electro-anatomical mapping system, in accordance with an embodiment of the present invention.

Electrical signals in the myocardium may be recorded by sensing electrodes disposed on diagnostic cardiac catheters. Such sensing electrodes may be disposed at a catheter distal end comprising a rigid backbone structure, or over stiff arms. A rigid backbone structure may be made, for example, of spines that are secured at both their ends to a shaft, e.g., assembled into a basket catheter. Alternatively, arms that are stiff enough can be held at one end only.

In some cases, however, a rigid distal end may be problematic. For example, while mapping the myocardium to acquire electrical signals, diagnostic catheters made of rigid structures or stiff members can trigger ectopic heartbeats (i.e., irregular heart rhythm due to a premature heartbeat) by mechanical contact with the tissue. There is also a risk of perforation of the myocardium by, for example, the edge of a stiff spine.

Embodiments of the present invention that are described hereinafter provide a multi-arm catheter comprising multiple flexible spines, referred to hereinafter as a 'flexible multi-arm catheter.' The flexible spines comprise a high density of diametrically opposing sensing electrode-pairs. The multiple flexible spines extend outward from a center of the distal end of the shaft that the soft catheter is fitted at and then curve inward towards the shaft and backwards in the proximal direction over the distal end of the shaft. Each flexible spine bends without being anchored at its other end, e.g., by embedding tensile material in the spine.

In other words, a given flexible spine has a respective first end that is connected to the distal end of the shaft and a respective second end that is free-standing and unanchored, wherein the spine is bent proximally such that the second end is more proximal than the first end.

Some disclosed embodiments utilize a flexible circuit board to construct spines that have electrodes on both the top-side and under-side (i.e., over diametrically opposing surfaces of the flexible circuit board). Such a geometry enables measuring signals from two opposing directions per each electrode-pair location. When the flexible spines are fully extended, the electrodes that face the shaft will typically not be in contact with tissue. These electrodes may be clinically significant when the spines are still partially advanced out of the sheath, when these 'interior' electrodes are still on the exterior side, and sensing may commence while the catheter is still in a compact form, being partially folded in the sheath.

In some embodiments, the circuit board is made of a flexible material that allows the circuit board to be tightly folded, in order to form the electrodes on two opposing sides. A thin material with high tensile strength, such as Vectran® or Ultra High Molecular Weight Polyethylene (UHMWPE), can be sandwiched between the two facets of the folded circuit board to force the flexible circuit board to bend. The resulting spine geometry provides additional structural and clinical safety, by avoiding contact of sharp edges with the myocardium.

Alternatively, or additionally, the flexible spine may include one or more high-tensile-strength fibers to control its bending, such as ones made of Liquid Crystal Polymer (LCP), Carbon Fiber, Fiberglass, and/or UHMWPE. In some embodiments, the flexible circuit has the electrodes conductive lines patterned as thin films and/or as an embedded yarn, in a way that maintains the structural flexibility of the flexible spine.

In some embodiments, the tensile strength of the material used for forcing the flexible circuit board to bend is greater than that of Nitinol alloys. Namely, for a same layer or a same fiber-thickness, the tensile force exerted by the layer or a fiber using one of the above listed materials, is higher than if made of one of Nitinol alloys. An example of catheter arms that are made of a Nitinol alloy, are the arms of a Pentaray® sensing-catheter, made by Biosense Webster, Irvine, California.

The disclosed flexible multi-arm catheter, whose arms are self-bending proximally and inwardly while being suspended from the distal end of the shaft, can accommodate any anatomy with high flexibility and with minimum stiffness. This design allows the physician to safely maneuver the catheter within a cardiac chamber and collect signals from tissue with less risk of ectopic beats or perforation. The soft multi-arm catheter thus expands the capabilities of a physician to diagnose certain cardiac disorders, especially in patients who are more vulnerable to side-effects described above of cardiac catherization. Moreover, the flexible multi-arm design can increase the accessibility to mapping of anatomy parts hard to access with existing designs.

System Description

FIG. 1 is a schematic, pictorial illustration of a catheter-based electro-anatomical mapping system 20, in accordance with an embodiment of the present invention. System 20 comprises a catheter 21, wherein a shaft 22 of the catheter is inserted into a heart 26 of a patient 28 through a sheath 23. The proximal end of catheter 21 is connected to a control console 31. In the embodiment described herein, catheter 21 may be used for any suitable diagnostic purposes, such as electrophysiological mapping and/or electro-anatomical mapping of tissue in heart 26.

Console 31 comprises a processor 38, typically a general-purpose computer, with suitable front end. Console 31 comprises also an interface circuitry 41 for receiving signals from catheter 21, as well as for connecting to other components of system 20 that processor 38 controls.

A physician 30 inserts shaft 22 through the vascular system of patient 28 lying on a table 29. As seen in an inset 25, catheter 21 comprises a soft multi-arm sensing catheter 40 fitted at the distal end of shaft 22 (after being advanced outside sheath 23). During the insertion of shaft 22, soft multi-arm catheter 40 is maintained in a collapsed configuration by sheath 23. By containing catheter 40 in a collapsed configuration, sheath 23 also serves to minimize vascular trauma along the way to target location. Physician 30 navigates soft multi-arm catheter 40 to a target location in heart 26 by manipulating shaft 22 using a manipulator 32 near the proximal end of the catheter and/or deflection from the sheath 23. Once the distal end of shaft 22 has reached the target location, physician 30 retracts sheath 23, or advances shaft 22, letting soft multi-arm sensing catheter 40 expand. The physician then operates console 31 so as sense signals using electrodes 24 (seen in FIG. 2) from tissue at the target location.

Although the pictured embodiment relates specifically to the use of a soft multi-arm sensing catheter 40 for electrophysiological sensing of heart tissue, the elements of system 20 and the methods described herein may additionally be applied in controlling multi-electrode ablation devices, such as circular ablation catheters, balloon ablation catheters, and multi-arm ablation devices.

Soft Multi-Arm Catheter with Diametrically Opposed Sensing Electrodes

Figure 2:
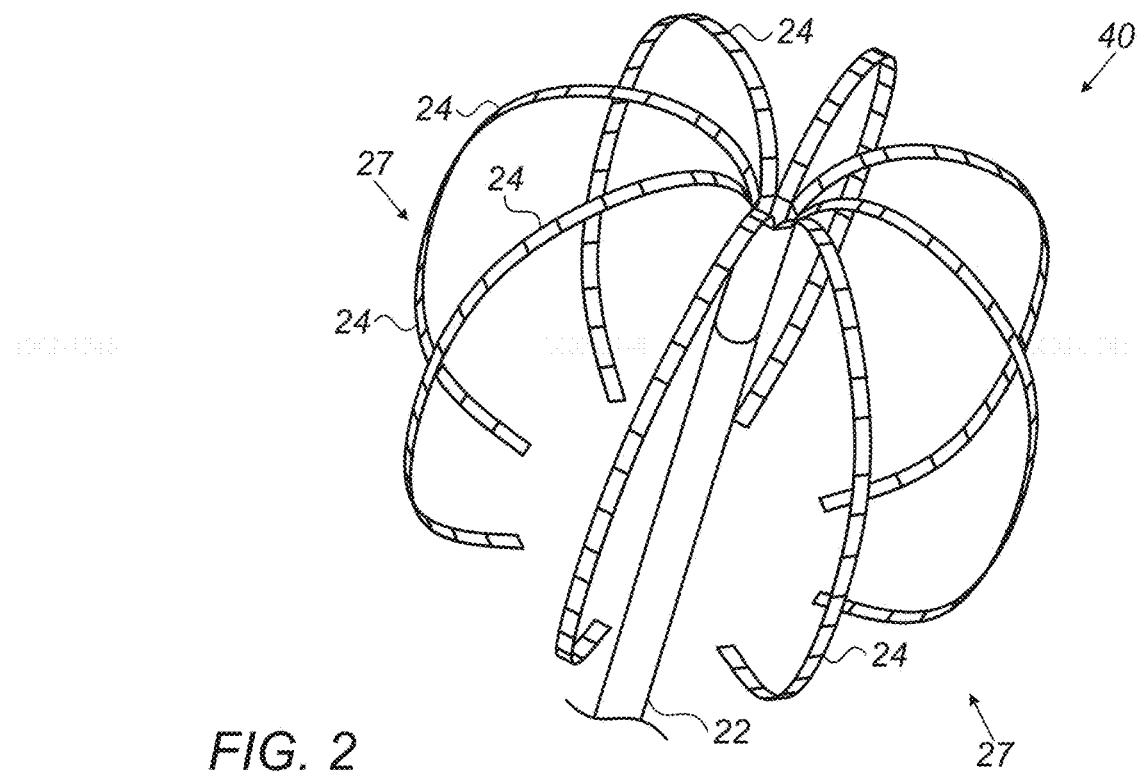
FIG. 2 is a schematic, pictorial view of a soft multi-arm catheter, in accordance with an embodiment of the present invention.

FIG. 2 is a schematic, pictorial view of soft multi-arm sensing catheter 40, in accordance with an embodiment of the present invention. As seen, soft multi-arm catheter 40 is fitted on a distal end of shaft 22. Catheter 40 is made of multiple flexible spines that extend diagonally outward from a center of the distal end of shaft 22. The spines then bend inwardly, in the proximal direction, over the distal end of shaft 22, with their other end free-standing and unanchored. A multiplicity of metallic elements in the form of rectangular sensing electrodes 24 are patterned over the two facets of flexible spines 27 so as to allow detection of signals from opposing directions.

Electrodes 24 that are facing the shaft after the spines fully expand may still be clinically significant prior to spines 27 being fully advanced out of the sheath. When spines 27 are partially advanced out, such interior electrodes are on the exterior side, and sensing may commence while the catheter is still in a compact form, being partially folded in the sheath.

Flexible spines 27 are practically semi-floating so as to gently accommodate an anatomy that the spines may come in contact with. The edges of spines 27 are pointing toward shaft 22 so as to avoid sharp contact of an edge of a spine with tissue.

Spines 27 are designed to apply elastic opposing force when pressed inward, for example when pressed against a surface of tissue. The strength of the elastic opposing force can be tuned during design and/or manufacturing, so as to optimize the flexibility of catheter 40. In an embodiment, the opposing elastic force is made strong enough to ensure firm contact of electrodes 24 with tissue, but still weak enough to minimize undesired events such as ectopic heartbeats upon mechanical contact of one or more spines 27 of catheter 40 with myocardium tissue.

The example illustration shown in FIG. 2 is chosen purely for the sake of conceptual clarity. Other configurations of flexible spines are possible. Alternative or additional patterns are possible, such as circular electrodes, as well as fitting additional types of patterned sensors or electrodes, e.g., ablative, strain, ultrasound, or any other suitable type of sensor or electrode. The cross-section of flexible spines 27 may vary in shape. The distribution and number of electrodes that may encompass the flexible spines may vary. For example, ring shaped electrodes may be disposed over flexible spines having a circular cross-section.

FIGS. 3A-3D are schematic views that exemplify manufacturing stages of flexible spines 27 comprising diametrically opposed electrodes, in accordance with some embodiments of the present invention. In general, the flexible spines and the electrodes comprise circuit board substrates, and metallic elements disposed on the circuit board substrates, respectively.

Figure 3A:
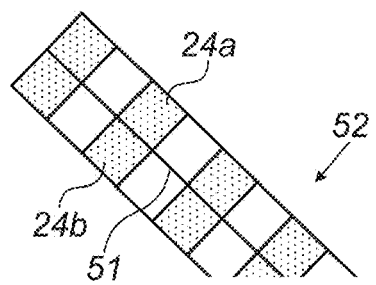
FIGS. 3A-3D are schematic views that exemplify manufacturing stages of flexible spines comprising diametrically opposed electrodes, in accordance with some embodiments of the present invention.

FIG. 3A shows a flexible circuit board 52 before being folded to form a spine 27. Sensing electrodes 24a and 24b are patterned over circuit board 52 with a folding line 51 separating them physically and electrically. Once flexible circuit board 52 will be folded along folding line 51, electrodes 24a and 24b will form the diametrically opposing electrodes geometry, as further described below.

Figure 3B:
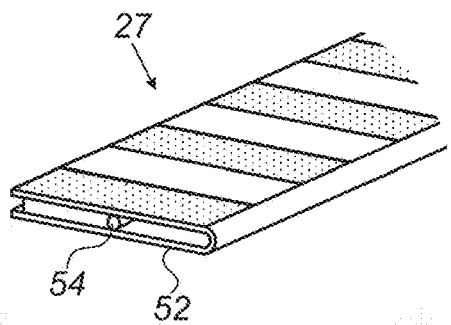

FIG. 3B shows a folded spine 27, which was made by folding circuit board 52 to achieve the diametrically opposing electrodes disposed on spine 27. The folded circuit board 52 wraps one or more tensile fibers 54 that run along the interior of the spine and provide the required structural strength and the tendency of spine 27 to bend as it is fixed on one of its ends.

Figure 3C:
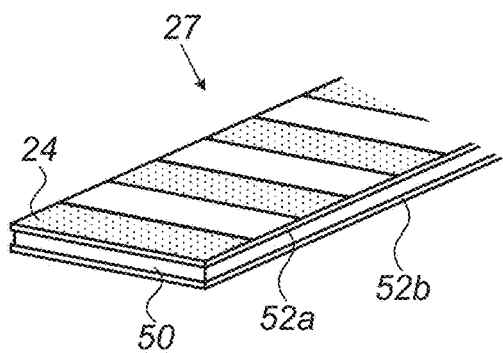

FIG. 3C shows another embodiment, in which flexible spine 27 is made of a layer of a tensile material 50, such as Liquid Crystal Polymer (LCP), Ultra High Molecular Weight Polyethylene (UHMWPE), para-aramid, carbon fiber, or glass fiber, which is laminated in between two flexible circuit boards 52a and 52b (that were made, for example, by cutting circuit board 52 into two along line 51). Sensing electrodes 24 are patterned over boards 52a and 52b to face opposite directions.

Figure 3D:
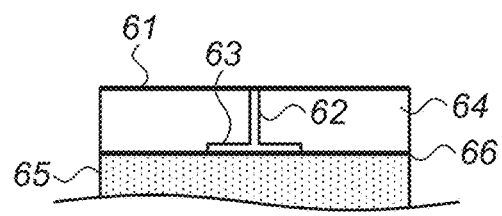

FIG. 3D provides a zoom-in cross-sectional view of a patterning scheme of electrode 24 on a flexible board 65. In an embodiment, electrode layer 61 is made of copper deposited on an insulating polyimide layer 64. Nickel is next deposited then onto the copper, and finally gold is deposited onto the nickel. In an alternative embodiment, electrode layer 61 is made of a Titanium Tungsten (TiW) seed layer sputtered onto insulating polyimide layer 64. Gold is next sputtered onto the seed layer, and then a final layer of gold is added in a plating process. A conductive trace 63 for electrode 24 is embedded underneath polyimide layer 64 so as to connect electrode 24 to system 20, wherein the polyimide insulating layer 64 isolates trace 63 from the electrode layer 61. In an embodiment, conductive trace 63 is made of copper encapsulated in a layer 66 of gold. A via 62 (a through hole) is formed (e.g., by etching or drilling through printed board 52) and plated with gold, so as to electrically connect electrode 24 with conductive trace 63. In an embodiment, via 62 extends deeper and all the way through flexible board 65, to connect the diametrically opposing electrodes (FIG. 3D shows only the one facet coated with an electrode, while for connecting the opposing electrode the via extends much deeper to reach the other electrode on the other facet of flexible board 65).

An adhesive layer 66 bonds polyimide layer 64 to flexible board 65 so as to provide additional endurance and aid in manufacturing the multiple layers.

The examples of manufacturing designs shown in FIGS. 3A-3D are chosen purely for the sake of conceptual clarity. In alternative embodiments, the patterned designs may include different number and types of electrodes. The processing technologies of the different parts and layers of flexible spines 27 may vary.

In an embodiment, a flexible multi-arm catheter is provided, having up to thirty-two sensing electrodes 24 (e.g., sixteen opposing pairs) patterned on each flexible spine 27. Cather 40 is made of eight spines, making the total number of sensing-electrodes disposed at catheter 40 up to 256 electrodes.

Figure 4:
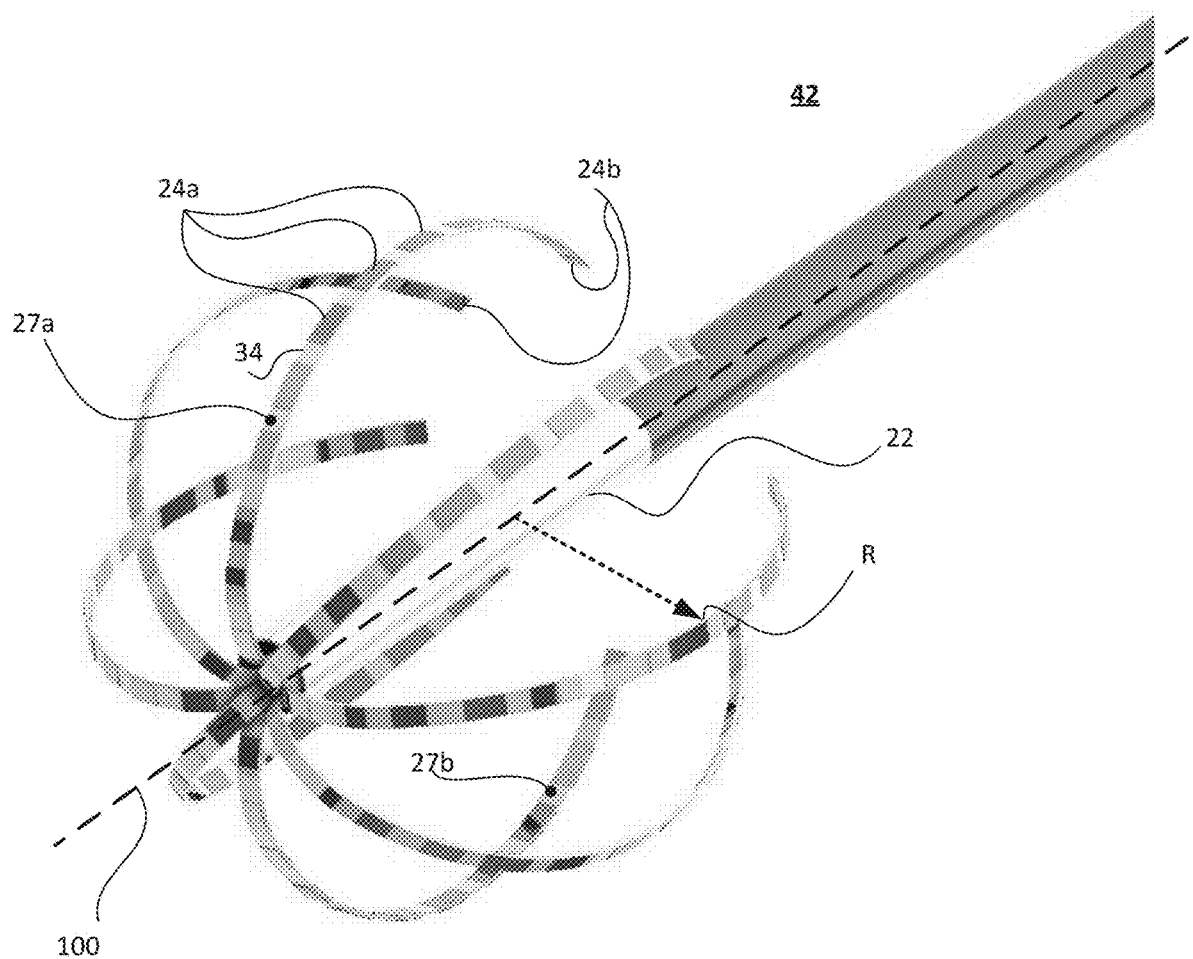
FIG. 4 is a schematic, detailed pictorial view of the soft multi-arm catheter of FIG. 2, in accordance with an embodiment of the present invention.

FIG. 4 is a schematic, detailed pictorial view of the soft multi-arm catheter of FIG. 2, in accordance with an embodiment of the present invention. For example, catheter 42 in FIG. 4 shows 12 electrode pairs 24 on each spine 27, each electrode pair 24 having an electrode 24a that faces away from a longitudinal axis 100 and an electrode 24b that faces the longitudinal axis 100. The spine 27 is configured such that when the spines 27 are fully extended from tubular shaft 22, a radius of curvature R can be conformed onto a portion of the interior surface 27b of the spine. As seen, spines 27 extend outward and then bend proximally and inwardly, relative to a longitudinal axis 100 of shaft 22. In an embodiment, tensile material 50 is configured to cause flexible spines 27 to bend freely at a preset radius of curvature R (i.e., the radius of the approximately circular arc shape that flexible spines 27 have) of about 0.40 inches with respect to a longitudinal axis 100, so as to have flexible spines 27 fit into a curved anatomy having similar typical size, such as of an ostium of a pulmonary vein.

In general, after catheter 40 is fully deployed, at least part of electrodes 24a will come in physical contact with tissue. Electrodes 24b, on the other hand, will typically not be in contact with tissue (rather, with blood only). Electrodes 24b may be clinically significant when the spines are still partially advanced out of the sheath, when these 'interior' electrodes are still on the exterior side, and sensing may commence while the catheter is still in a compact form, being partially folded in the sheath. Additionally, electrodes 24b may be used for the collection of background (e.g., far-field) electrophysiological signals, which processor 41 may utilize for the analysis of tissue electrophysiological signals from respective electrodes 24a.

In an embodiment, the size of electrodes 24a and 24b is both about 0.040 by about 0.027 inches, in width times length, respectively. The length of gap 34 between neighboring electrodes 24 is about 0.030 inches. The size of electrodes and gaps is designed such that it provides the medically required spatial resolution of intra-cardiac measured electrophysiological signals. The exemplary configurations described and illustrated herein allow for the elimination of a rigid backbone member such as a Nitinol wire in the spine while allowing detection of signals from both side of spine 27 via outer electrode 24a and inner electrode 24b (FIG. 4) for each electrode pair 24. This can be achieved by configuring each spline to have a flexible circuit substrate. The substrate has conductive surfaces on the outer surface of the substrate as electrodes. By using the thin flexible circuit with a suitable tensile member (e.g., polymeric fiber) disposed between the surfaces, a physician can maneuver the spines 27 in the heart and collect signals regardless of the orientation of the spines 27 as well as a lower risk of complications due to the spine members.

Although the embodiments described herein mainly address cardiac electrophysiological mapping and/or electroanatomical mapping, the methods and systems described herein can also be used in other applications, such as otolaryngology or neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical instrument, comprising:
a shaft for insertion into a body of a patient;
multiple flexible spines, each multiple flexible spine comprising a respective circuit board substrate, the multiple flexible spines having respective first ends that are connected to a distal end of the shaft and respective second ends that are free-standing and unanchored, the circuit board substrates each comprising a folding line, wherein the multiple flexible spines are bent proximally such that the second ends are more proximal than the first ends, and wherein each of the multiple flexible spines comprises a tensile layer configured to cause the multiple flexible spines to bend proximally; and
multiple electrodes disposed over the multiple flexible spines, the multiple electrodes comprising multiple pairs of first and second electrodes; and
wherein the circuit board substrates are folded along the folding line so that, for each respective pair of first and second electrodes, the first electrode and the second electrode are (i) disposed over diametrically opposing facets of the respective circuit board substrate, (ii) separated electrically along the folding line, and (iii) electrically connected to one another by a via extending through the respective circuit board substrate.

2. The medical instrument according to claim 1, wherein each of the tensile layers comprises one or more tensile fibers configured to cause the multiple flexible spines to bend proximally.

3. The medical instrument according to claim 1, wherein a tensile strength of the tensile layer is greater than that of a Nitinol alloy layer of same dimensions.

4. A manufacturing method, comprising:
producing multiple flexible spines having multiple electrodes disposed thereon, the multiple electrodes comprising multiples pairs of first and second electrodes; and
mounting the multiple flexible spines at a distal end of a shaft, wherein the multiple flexible spines have respective first ends that are connected to the distal end of the shaft and respective second ends that are free-standing and unanchored, wherein the multiple flexible spines are bent proximally such that the second ends are more proximal than the first ends, and wherein each of the multiple flexible spines comprises a tensile layer configured to cause the flexible spine to bend proximally;

wherein producing the multiple flexible spines comprises disposing the multiple electrodes on circuit board substrates, each circuit board substrate comprising a folding line; and wherein producing the multiple flexible spines comprises folding the circuit board substrates along the folding line so that, for each respective pair of first and second electrodes, the first and second electrode are (i) disposed over diametrically opposing facets of the respective circuit board substrate, (ii) separated electrically along the folding line, and (iii) electrically connected to one another by a via extending through the respective circuit board substrate.

5. The manufacturing method according to claim 4, wherein producing the multiple flexible spines comprises disposing the multiple electrodes over diametrically opposing surfaces of the multiple flexible spines.

6. The manufacturing method according to claim 4, wherein producing the multiple flexible spines comprises fitting one or more tensile fibers in each of the multiple flexible spines, so as to cause the multiple flexible spines to bend proximally.

7. The manufacturing method according to claim 4, wherein producing the multiple flexible spines comprises including a tensile layer with tensile strength that is greater than that of a Nitinol alloy layer of same dimensions.

8. A manufacturing method, comprising:
patterning electrodes and conductive lines on multiple flexible circuit boards, the electrodes comprising pairs of first and second electrodes;
folding the flexible circuit boards along respective folding lines of the circuit boards, over one or more fibers made of a tensile material, such that the one or more fibers become sandwiched between two diametrically opposing facets of the patterned flexible boards, so as to form multiple flexible spines, and such that, for each respective pair of first and second electrodes, the first electrode and the second electrode are (i) disposed over diametrically opposing facets of respective the circuit board substrate, (ii) separated electrically along the folding lines, and (iii) electrically connected to one another by a via extending through the respective circuit board substrate; and
mounting the multiple flexible spines at a distal end of a shaft, wherein the multiple flexible spines have respective first ends that are connected to the distal end of the shaft and respective second ends that are free-standing and unanchored, wherein the multiple flexible spines are bent proximally such that the second ends are more proximal than the first ends, and wherein a tensile layer included in each of the multiple flexible spines is configured to cause the multiple flexible spines to bend proximally.

9. A medical instrument, comprising:
a catheter shaft extending along a longitudinal axis from a proximal end to a distal end;
multiple flexible spines extending out of the catheter shaft from the distal end, each flexible spine comprising a folded flexible circuit board that includes: a respective first end that is connected to the distal end of the catheter shaft, a respective second end that is free-standing and unanchored, and a folding line the folded flexible circuit board is folded along;
a first plurality of electrodes disposed on a surface of each of the multiple flexible spines, the first plurality of electrodes facing the longitudinal axis; and
a second plurality of electrodes disposed on a surface of each of the multiple flexible spines, the second plurality of electrodes facing away from the longitudinal axis, the second plurality of electrodes being separated electrically from the first plurality of electrodes along the folding line, and each electrode of the second plurality of electrodes being electrically connected to a respective electrode of the first plurality of electrodes by a via extending through the respective folded flexible circuit board; and
a tensile member disposed between the folded flexible circuit board having tensile strength greater than 895 MPa.

10. The medical instrument of claim 9, wherein each of the multiple flexible spines of the multiple flexible spines is configured such that when each of the multiple flexible spines is fully extended from the catheter shaft, a radius of curvature R can be conformed onto a portion of the surface of each of the multiple flexible spines facing the longitudinal axis.

11. The medical instrument of claim 9, wherein the tensile member causes each of the multiple flexible spines to bend freely along a radius of curvature R of about 0.40 inches with respect to the longitudinal axis.

\* \* \* \* \*